(12) United States Patent
McKenna et al.

(10) Patent No.: US 6,394,094 B1
(45) Date of Patent: May 28, 2002

(54) METHOD FOR INJECTION MOLDING MANUFACTURE OF CONTROLLED RELEASE DEVICES

(75) Inventors: Michelle McKenna, Perkasie, PA (US); Angela Reid-Haqq, Highstown, NJ (US); John F. Cline, Westfield, NJ (US); Edward J. Gabrielski, Bound Brook, NJ (US)

(73) Assignee: Enhance Pharmaceuticals, Inc., Plainsboro, NJ (US)

( * ) Notice: Subject to any disclaimer, the term of this patent is extended or adjusted under 35 U.S.C. 154(b) by 0 days.

(21) Appl. No.: 09/304,285

(22) Filed: May 3, 1999

Related U.S. Application Data
(60) Provisional application No. 60/083,943, filed on May 1, 1998.

(51) Int. Cl.[7] .................................................. A61F 6/06
(52) U.S. Cl. ........................ 128/830; 128/832; 128/834
(58) Field of Search .................................. 128/830, 831, 128/837; 264/255, 513; 425/130

(56) References Cited

U.S. PATENT DOCUMENTS

| | | | |
|---|---|---|---|
| 3,920,805 A | * 11/1975 | Roseman ................... 128/832 |
| 3,921,856 A | 11/1975 | Langecker | |
| 4,292,965 A | 10/1981 | Nash et al. | |
| 4,376,625 A | 3/1983 | Eckardt | |
| 4,459,257 A | 7/1984 | Baciu | |
| 4,774,047 A | 9/1988 | Nakamura et al. | |
| 4,822,616 A | 4/1989 | Zimmermann et al. | |
| 4,863,665 A | 9/1989 | Schad et al. | |
| 4,888,074 A | 12/1989 | Pocknell | |
| 4,935,191 A | 6/1990 | Baxi | |
| 4,990,301 A | 2/1991 | Krishnakumar et al. | |
| 5,028,226 A | 7/1991 | De'ath et al. | |
| 5,030,077 A | 7/1991 | Orimoto et al. | |
| 5,088,505 A | 2/1992 | De Nijs | |
| 5,104,305 A | 4/1992 | Kawaguchi et al. | |
| 5,131,183 A | 7/1992 | Orimoto et al. | |
| 5,141,695 A | 8/1992 | Nakamura | |
| 5,174,932 A | 12/1992 | Johnson et al. | |
| 5,228,456 A | * 7/1993 | Karg ........................... 128/837 |
| 5,232,710 A | 8/1993 | Miyazawa et al. | |
| 5,558,824 A | 9/1996 | Shah et al. | |
| 5,558,877 A | 9/1996 | Matlin et al. | |
| 5,595,799 A | 1/1997 | Beck et al. | |
| 5,637,328 A | 6/1997 | Shah et al. | |
| 5,651,998 A | 7/1997 | Bertschi et al. | |
| 5,660,187 A | * 8/1997 | Hiller ......................... 128/832 |
| 5,694,947 A | * 12/1997 | Lehtinen ...................... 128/832 |
| 5,788,980 A | 8/1998 | Nabahi et al. | |
| 5,798,069 A | 8/1998 | Bertschi et al. | |
| 6,063,325 A | * 5/2000 | Nahill ......................... 264/513 |

FOREIGN PATENT DOCUMENTS
EP          077669          6/1997

* cited by examiner

*Primary Examiner*—Michael A. Brown
(74) *Attorney, Agent, or Firm*—Gibbons, Del Deo, Dolan Griffinger & Vecchione

(57) ABSTRACT

Thermoset polymer controlled release devices are produced by an injection molding of two or more polymers in a mold to produce a core surrounded by a sheath. The polymers may be injected sequentially or simultaneously.

36 Claims, 10 Drawing Sheets

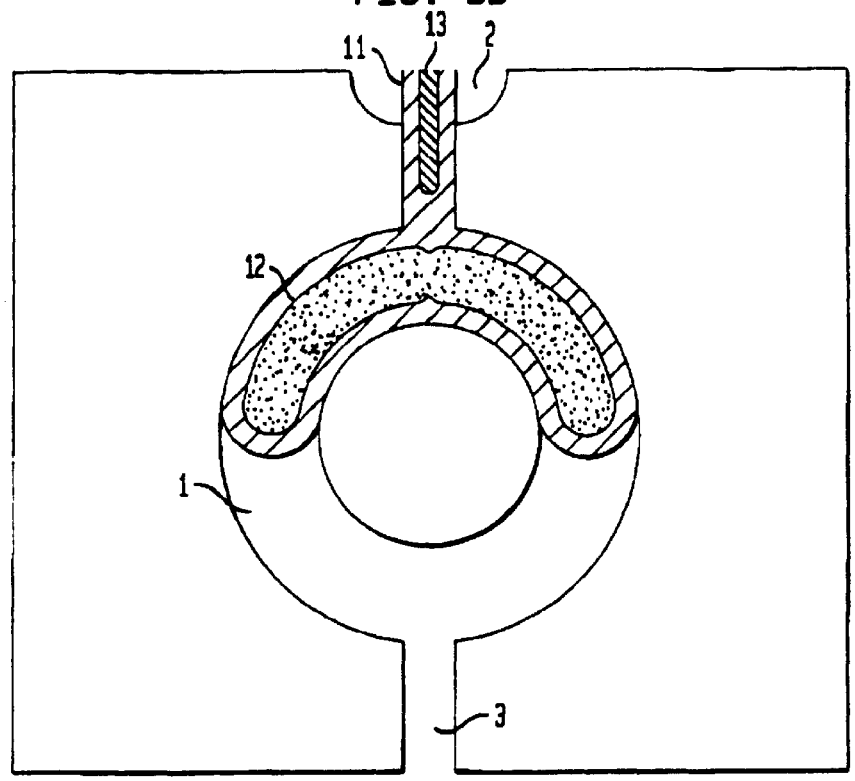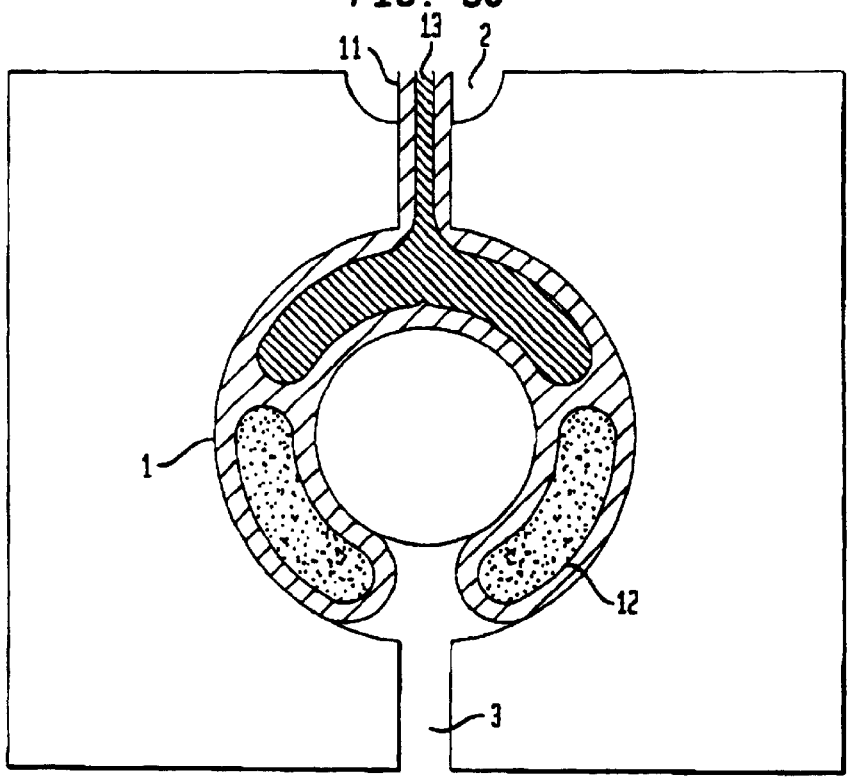

METHOD FOR INJECTION MOLDING MANUFACTURE OF CONTROLLED RELEASE DEVICES

This appln claims benefit of Prov. No. 60/083,943 filed May 1, 1998.

BACKGROUND OF THE INVENTION

Injection molding of thermoplastic and elastomeric materials has been commonplace for several decades. Injection molding equipment has advanced from basic one-component, single cavity parts to multi-component, multi-cavity parts. For example, U.S. Pat. No. 4,376,625 discloses injection molding equipment for molding a single part from two different resins at once. Furthermore, gas-assisted plastic molding techniques have been developed to fabricate hollow parts as shown in U.S. Pat. Nos. 4,935,191 and 5,174,932. In some cases the mold cavity is pressurized in order to provide finer control for the plastic melt flow as described in U.S. Pat. No. 5,558,824. These techniques have been applied to advanced engineering problems for automotive and consumer products. For example, two-component injection molding can be used to apply a coating of virgin resin around a core of recycled, reground resin. However, co-injection techniques have not been applied to the fabrication of controlled release devices for use in controlled release of a substance to the body.

Controlled release devices deliver a specific amount of an active agent in a predictable fashion. There are several potential mechanisms for release of the active agent from the device, including, but not limited to, diffusion, osmosis, magnetism, solvent swelling, or erosion. Controlled release products have been used to deliver many different agents including, but not limited to, soaps, insecticides, and especially drugs. Substantial effort has been devoted to developing controlled release pharmaceutical dosage forms. Controlled release of pharmaceuticals encompasses a broad array of products including extended release oral dosage forms, transdermal patches, intravaginal rings (IVRs), implants, and intrauterine devices (IUDs).

Controlled release devices utilizing diffusion mechanisms form a large class of pharmaceutical dosage forms, including transdermal devices, implants and intravaginal rings. Diffusion based controlled release designs typically have a multi-laminar structure. This feature of the design frequently involves one or more rate controlling membranes or layers which surround a core reservoir containing the active chemical agent, and which function to control or moderate the rate at which the substance diffuses out of the core. A significant challenge to the manufacture of a controlled release product is the efficient application of the rate controlling membrane. Multiple step manufacturing processes are common and usually necessary to produce a device having a rate controlling membrane. Specifically, manufacturing processes for controlled release vaginal rings have included intertwined tubes described in U.S. Pat. No. 4,237,885; solvent swelling of components before assembly described in U.S. Pat. No. 4,292,965; forming an extruded tube described in U.S. Pat. No. 4,888,074; and sequential insert molding described in U.S. Pat. No. 3,920,805. All of these methods require multiple steps, and some employ hazardous solvents. The inability to efficiently manufacture vaginal rings having a rate controlling membrane surrounding a core, has been a significant reason this type of dosage form has not been widely available commercially. Therefore, methods which can reduce the number of steps required to manufacture a controlled release device, and specifically a vaginal ring, are especially valuable.

SUMMARY OF THE INVENTION

Controlled release devices provide predictable and reproducible drug release kinetic profiles for prolonged release of a therapeutic agent. The present invention provides methods for co-injection manufacture of controlled release devices having various layers or segments of materials. The methods can be utilized to mass produce products containing a variety of active agents, products having multiple layers of different polymeric materials, and products having different shapes. Two or more layers or segments are possible, and the layers or segments may contain different active agents, or be comprised only of a polymeric material. The active agent may be any agent capable of diffusing from the polymeric material. The invention may be particularly useful for controlled release of active agents such as industrial chemicals, cosmetic fragrances, growth factors, antimicrobials, metallic ions, cytotoxins, peptides, prodrugs, natural substances, cytokines, hormones, or other pharmaceutical agents.

The invention utilizes novel methods for injecting two or more materials, and thermoset materials in particular, into a mold in order to efficiently produce a controlled release device. An advantageous aspect of the invention is the ability to reliably reproduce the application of a rate controlling membrane to a core containing an active agent, whereby the device will release the agent in a predictable fashion. Materials can enter the mold through one or more gates and exit the mold through one or more runners. The materials may be sequentially injected into a mold with one or more injection nozzles or syringes. Alternatively, the materials may be simultaneously injected into the mold using a co-injection nozzle having two axially symmetric openings. The mold itself may be capable of producing more than one device in a given injection cycle by the use of multiple mold cavities. The mold design imparts the physical shape of the product, for example, a ring, a rod, or any other desired shape. However, although the mold design is important to the development of a specific product and process, various mold designs are commonplace in the art, and may be selected or adapted as desired.

In a simple embodiment, co-injection of two materials is effected by using two separate, single material injection nozzles, with a set time delay between injection of the first material and injection of the second material. A more advanced co-injection method utilizes a co-injection nozzle which provides for simultaneous, as well as sequential, entry of multiple materials into a single mold gate.

Three or more materials may be injected into a mold through a single gate. This type of flow pattern can be achieved by splitting the material feed so that more than one material is delivered by one co-injection nozzle. Instead of simply feeding material into the circular nozzle orifice from one source, there may be two sources having appropriate valving and integrated electromechanical controls such that two different materials can be sequentially fed into one orifice. Another adaptation is to split a circular orifice, for example into two semicircles.

Devices containing two or more different active agents, with a separate rate controlling membrane for each agent, may also be produced using a mold having multiple gates. Furthermore, the membrane thickness used to encapsulate each active agent may be different. In addition, the invention can be applied to shapes other than rings, for example by using a rod shaped mold.

DETAILED DESCRIPTION OF THE INVENTION

Figure 1A:
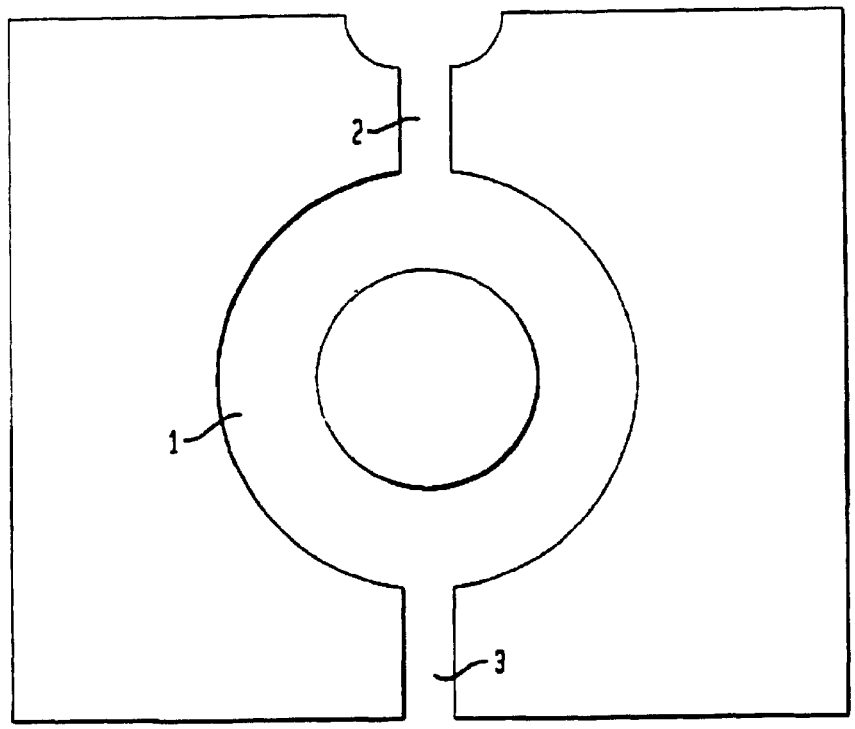
FIG. 1: Material Flow Diagram For Sequential Co-Injection of a Vaginal Ring

The invention involves co-injection methods for producing controlled release devices. The controlled release devices produced in accordance with the present methods comprise a core of material which contains at least one active agent or other substance which is to be released, surrounded by a sheath or outer membrane, which serves to control or moderate the rate of diffusion of the substance from the core. The core material may be substantially liquid, or may contain a substantial amount of air, or may be a liquid suspension of the active agent, or may be a powder form of the active agent. The core material may or may not crosslink. The outer sheath or outer membrane is a thermoset material which crosslinks upon the application of heat.

Utilizing precise coordination of the injected volumes, mold temperature, injection rates, and injection time delays, more control over the co-injection process is possible and more complex products can be produced. For example, a time delay between injection of two materials can be employed. If the outermost material is injected first, and allowed a brief residence time in the mold prior to injection of the core material, then the outer material will partially cure and become more viscous. This technique may be useful in order to maintain a distinct separation of the two materials in the finished product, or to vary the applied membrane thickness. Furthermore, if an excess amount of outer material is injected first followed by core material, it is possible to produce a segmented product having core material present in a portion of the finished product, but not throughout. This technique is useful to adjust the delivery rate of the active ingredient, or to produce products containing multiple active ingredients.

The injection process may involve the simultaneous co-injection of two materials into a mold cavity, or may involve sequential injection of materials over specified intervals. In a preferred embodiment, two separate injection nozzles may be utilized. The first material is injected into the mold through one nozzle and allowed to remain for a desired interval before the second material is injected through the second nozzle. During the interval, the first material begins to undergo cross-linking. This process may be hastened by heating the mold. In a heated mold, the portion of the material which contacts the mold will begin cross-linking, thereby increasing the viscosity of the outer layer of the material, a phenomenon referred to as "skinning". As a result, when the second material is injected, the differential viscosities will result in laminar flow between the two polymers, creating a sheath formed by the first polymer surrounding a core containing one or more active agents.

In another preferred embodiment, a single injection nozzle has two or more separate openings to accommodate the two or more materials. In one such nozzle, the openings are arranged such that the first material completely surrounds the second material. This may be accomplished by using a circular nozzle opening concentrically disposed with a surrounding annular nozzle opening. As the two materials are injected into the mold using a nozzle of this design, the outermost material from the annular nozzle encapsulates the inner material from the circular nozzle. In this embodiment, injection of the outermost material is started prior to concurrent injection of both materials, and before the materials reach the mold's exit runner the flow of the innermost material is halted. By careful timing of the intervals during which each material is injected, an encapsulating membrane can be formed around the core material containing an agent to be released.

Controlled release devices in accordance with the present invention may be produced in any desired shape which is suitable for its intended use. In a preferred embodiment, a controlled release device is produced having a toroidal shape, which is particularly suited for use as an intravaginal ring. Intravaginal rings are commonly used for the controlled release of an agent such as a hormone. In another embodiment, the device may be in the form of a substantially cylindrical rod.

Controlled release devices in accordance with the present invention may be produced by co-injection molding of any of various thermoset materials. Preferred materials are elastomers, and particularly preferred are silicone co-polymers. In particular, vaginal rings may be produced by injection of silicone polymers, which may include various catalysts or cross-linking agents. Such silicone compounds, catalysts and crosslinking agents are commonplace in the art and are described in U.S. Pat. No. 4,888,074. A silicone composition may be an organo-silicone compound capable of crosslinking, with or without the presence of crosslinking agents. Such crosslinking may be performed at elevated or at ambient temperatures. The elastomer-forming silicone composition may crosslink only very slowly at room temperature and have a greatly increased crosslinking rate at elevated temperatures of the order of 35° to 200° C. Various methods may be employed to maintain separation between polymer containing catalyst and polymer containing cross-linker prior to polymerization. Preferred silicones for injection molding are available in two-part systems, in which one portion of the polymer contains an organoplatinum catalyst and another portion of the polymer contains the cross-linking agent.

Controlled release devices in accordance with the present invention may also be produced by co-injection molding of other thermoset materials, including, but not limited to, reactive resins and phenol-formaldehyde compounds. Crosslinking of these materials typically involves the presence of double bonds which react with the application of elevated temperatures to form three-dimensional networks.

The organopolysiloxanes used are such that the composition is capable of being injected and at least one of the materials has sufficiently high viscosity to resist mixing through turbulent flow after injection and before crosslinking has fully developed. Elastomer-forming silicone compounds comprising organopolysiloxanes having silicon-bonded hydroxyl groups, which may be crosslinked to elastomers by the addition of a crosslinking agent and a condensation catalyst, may be used. In such compounds the organopolysiloxane is generally a polydiorganosiloxane having terminal silanol groups. The crosslinking agent may be, for example, an alkoxy silane or an alkyl polysilicate, e.g. methyl trimethoxysilane or ethyl polysilicate, or it may be an alkylhydrogen polysiloxane, e.g. a polymethyhydrogensiloxane. A variety of well-known catalysts may be employed, the organic metal compounds e.g. stannous octoate, dibutyltin dilaurate, alkyl titanates and titanium chelates being illustrative of these. The use of such catalysts should be controlled, since volatile by-products of the crosslinking action with catalysts may lead to voids in the rings unless suitably controlled. Also, the tin catalysts employed in such compositions are less favored from a toxicity viewpoint.

Preferred elastomer-forming silicone compositions are those which crosslink, for example upon heating, without production of volatile by-products. The absence of volatile by-products simplifies the manufacturing process. This permits a more accurate manufacture of the rings with respect to their shape and size. Due to the possibility of formulating compositions which crosslink at lower temperatures, as may be desirable when certain thermally sensitive therapeutic agents are employed, the most preferred compositions are those silicone compositions which crosslink through reaction of unsaturated vinyl groups. These compositions comprise one or more organopolysiloxanes having per molecule at least two silicone-bonded groups having aliphatic unsaturation, an organosilicon cross-linking compound having at least two silicon-bonded hydrogen atoms and a catalyst e.g. a platinum compound or complex which promotes the reaction between unsaturated groups and silicon-bonded hydrogen groups. The platinum containing compound or complex is for example chloroplatinic acid, platinum acetylacetonate, a complex of platinous halides with unsaturated compounds such as ethylene, propylene, organovinylsiloxanes and styrene, methyldiplatinum and $Pt(CN)_3$. The composition may include a catalyst inhibitor, for example an alkynyl compound such as an acetylenically unsaturated secondary or tertiary alcohol for example ethynyl cyclohexanol. The aliphatically unsaturated groups are preferably olefinically unsaturated. The organopolysiloxane used in such a composition typically is a high molecular weight polysiloxane of grease-like consistency. The organosilicon compound used in such a composition is typically an organohydrogensiloxane having an extrusion rate of 5–500 gallons per minute.

The ingredients of the composition are chosen so that the composition typically cures at temperatures between about 100° C. and 150° C. and so that the cured elastomer has a durometer of ASTM shore A hardness in the range 10 to 100, more preferably about 35. Compositions of this type are well known in the art (see for example British Patent Specifications Nos. 1 090 122, 1 141 868 and 1 409 223) and are commercially available. The elastomer-forming compositions may also comprise other ingredients, for example fillers and plasticisers. The curing temperature is preferably lower than the melting point of any active substance contained in the elastomer.

A plurality of mold cavities may be incorporated into a single mold, or may be placed adjacent to one another to enable the simultaneous production of a number of rings in a single operation. Molds may be constructed of hardened carbon steel or a stainless steel.

During co-injection of two or more materials, as the materials emerge from the entrance gate and enter the mold cavity, they fill the void in the mold cavity while maintaining a distinct separation. The polymers used in the invention will typically flow into the mold cavity according to commonly understood fluid dynamic principles such as those described in University Physics, Seers et al., Fifth Edition, pages 233–243, incorporated herein by reference. The materials used in the present invention are substantially incompressible, viscous, and exhibit laminar flow when injected into a mold cavity. Separation will be maintained as long as the two materials are not readily miscible, for example, by virtue of their viscosity's or chemical properties. Polymers useful in the invention will typically exhibit a viscosity in the range of 100 to 10,000,000 centipoise, preferably in the range of 10,000 to 1,000,000 centipoise. Also mold design characteristics are important to maintain laminar flow behavior. Introduction of mold features which create turbulence will reduce the predictability of the process. The rate at which the material fills the cavity is directly related to the viscosity and the injection pressure and the size of the entrance gate. For materials exhibiting little compressibility, fluid dynamics predicts a material velocity which is inversely proportional to the cross-section area orthogonal to flow; therefore, the larger the cavity, the slower the material will fill the cavity. However, as long as the flow is laminar, the two materials will remain separated as they fill the cavity and exit the runner. The volumetric input ratio of the two materials will determine the relative amounts of the materials in the finished product, and can easily be calculated.

The relative viscosities of the materials being co-injected will affect the thickness of layers in the resulting controlled release device. For example, a more viscous starting material will generally yield a thicker laminar layer. Thus, the thickness of the rate-controlling membrane on a controlled release device, for example, may be increased or decreased by using a respectively more or less viscous silicone. Controlled release devices may be made with silicones having varying initial viscosities to achieve a desired thickness of the layers.

Temperature also affects viscosity. Heating causes the elastomer to begin the curing process, thereby increasing the viscosity of the outer layer in contact with the mold resulting in a thicker membrane after the second material has been injected. Relative thickness of various layers in a controlled release device may thus be controlled by adjusting the temperature of the mold and the various times during which the polymers remain in the mold during the injection process.

Controlled release devices having a substantially liquid core with an active agent within a surrounding sheath may also be produced. A first elastomer is injected into the heated mold and allowed to partially cure. Subsequently, the liquid core containing the active agent is injected.

In the alternative manufacturing examples cited previously, nearly perfect uniformity is expected for the membrane thickness. However, maintenance of perfect membrane thickness uniformity is not essential to the overall performance of a controlled release device. The release of an active agent over time will remain predictable, as long as the mean membrane thickness is controllable and reproducible.

Additional, more complex, co-injection techniques can be used for production of segmented products or products having multiple active ingredients. For example, multiple materials can be injected into the mold through two or more gates using two or more separate nozzles. In addition, each nozzle can deliver one or more materials. In the single nozzle case, the nozzle could deliver three or more materials. For example, the circular center opening described previously could be divided into two halves. In this configuration, the resulting product would have a multiple component core encapsulated by a single material. Two separate nozzles can be used to segment the product, and in this configuration, the encapsulating material for each segment could be different.

To produce a ring suitable for intravaginal placement, silicone polymer is injected into a toroidal mold cavity. The mold cavity may have one or more entrance gates or openings through which polymer is injected into the cavity. The mold cavity will also have one or more exit runners through which air is expressed from the cavity as polymer fills the cavity and through which excess polymer may exit the mold cavity once the cavity is filled. Alternatively, air may be removed by vacuum prior to injection. A mold cavity may have any number of entrance gates and exit runners.

Figure 1B:
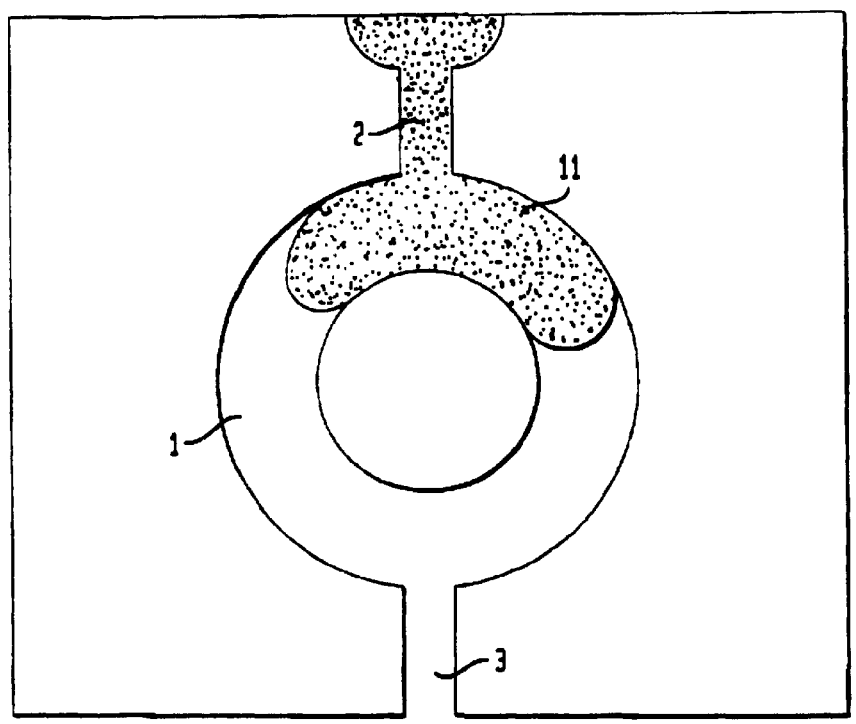
Figure 1C:
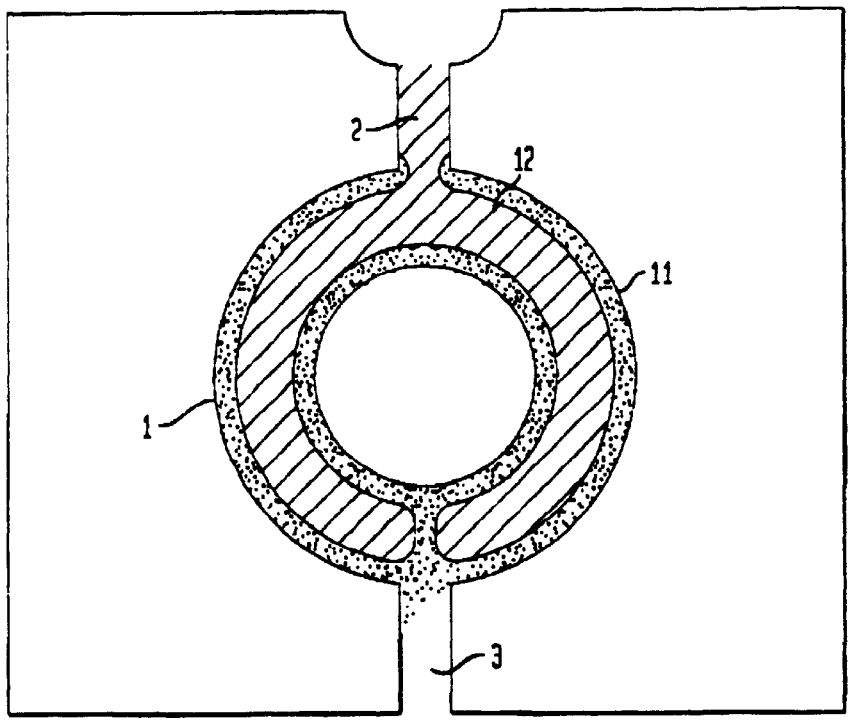

FIG. 1a shows a mold in top planar view illustrating a toroidal mold cavity 1 having an entrance gate 2 and an exit runner 3. FIGS. 1b and 1c show a first sheath polymer 11 and a second core polymer 12 being sequentially co-injected into mold cavity 1. FIG. 1b illustrates the injection of first polymer 11 at time $t_1$ after the polymer has emerged from entrance gate 2 and filled a portion of the cavity. The mold is heated so as to promote cross-linking of the polymer, thus increasing the viscosity of the polymer. FIG. 1c shows sheath polymer 11 and core polymer 12 at time $t_2$ where mold cavity 1 is substantially filled. The separation between the polymers is maintained as flow continues through the mold, in accordance with fluid dynamic principles outlined above.

Figure 2A:
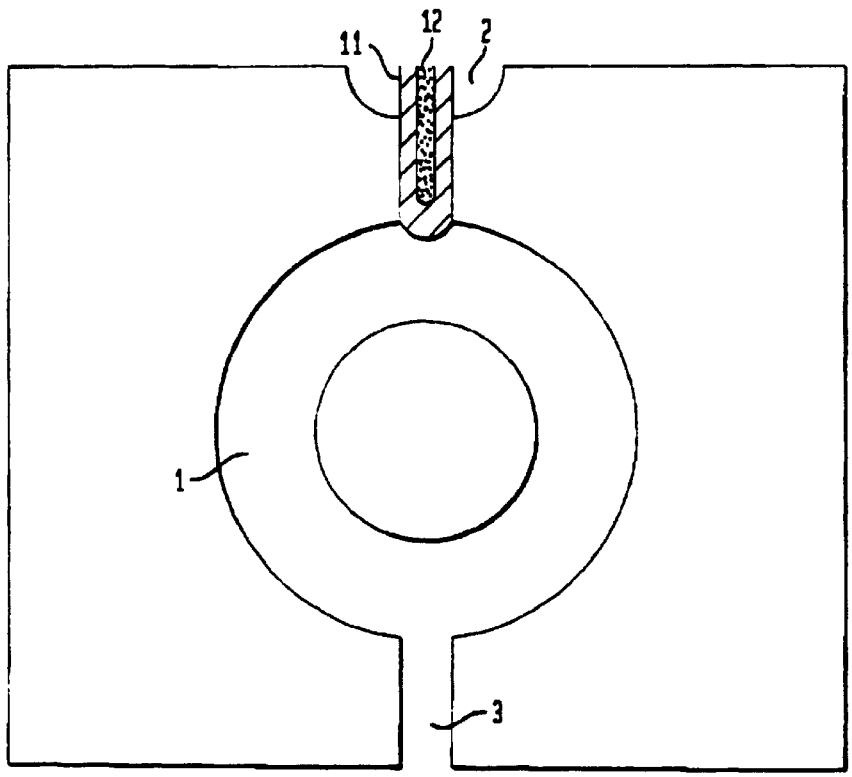
FIG. 2: Material Flow Diagram For Simultaneous Co-Injection of a Vaginal Ring
Figure 2B:
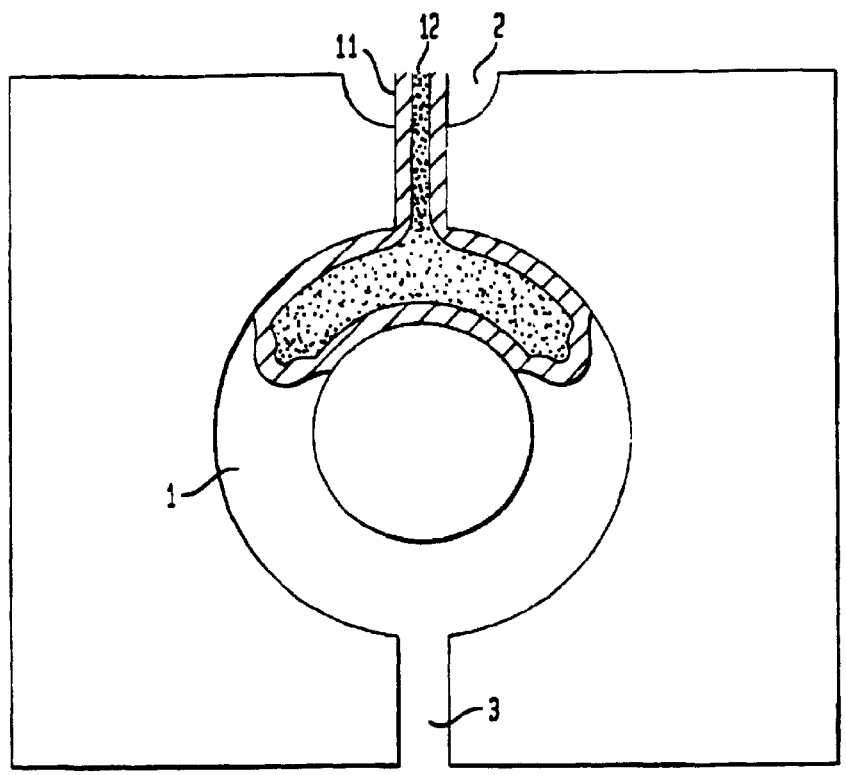
Figure 2C:
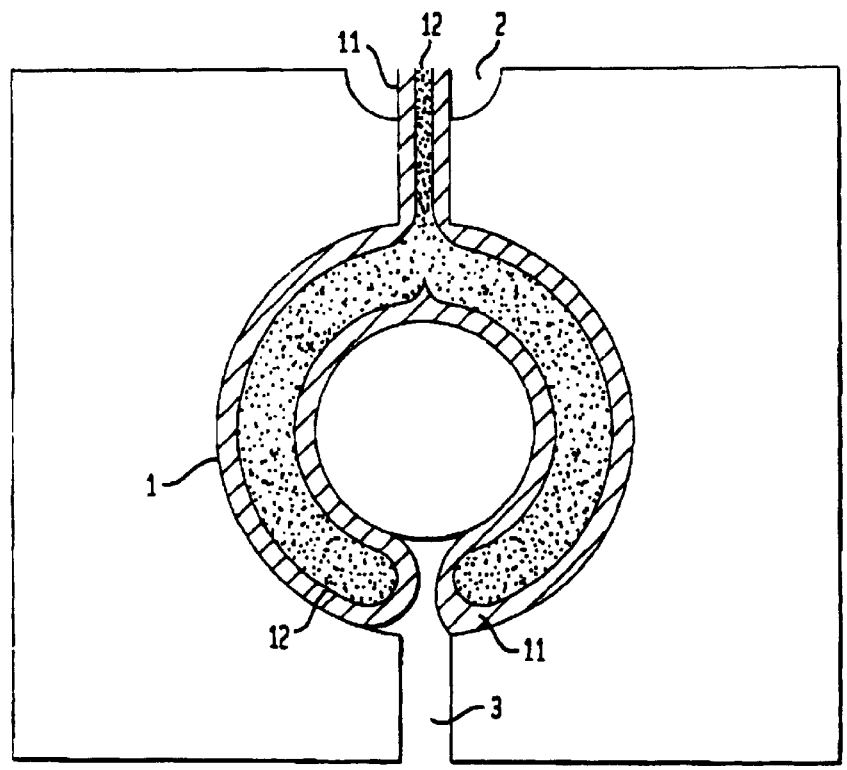
Figure 2D:
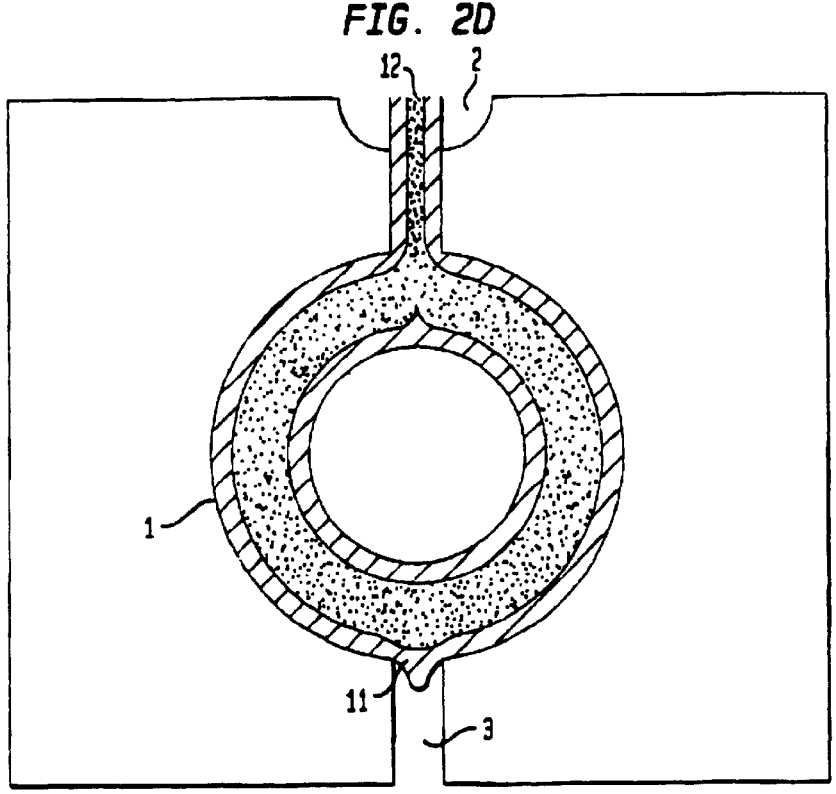

FIG. 2a shows a first sheath polymer 11 and a second core polymer 12 being simultaneously co-injected into entrance gate 2 at time $t_1$. The separation between the polymers will be maintained as flow continues through the mold, in accordance with fluid dynamic principles outlined above. FIG. 2b shows sheath polymer 11 and core polymer 12 at time $t_2$ continuing through mold cavity 1. FIG. 2c shows the polymers 11 and 12 at time $t_3$ approaching the exit runner 3. FIG. 2d shows the polymers 11 and 12 at time $t_4$, where polymer 11, comprising the sheath layer, filling the exit runner 3.

Figure 3A:
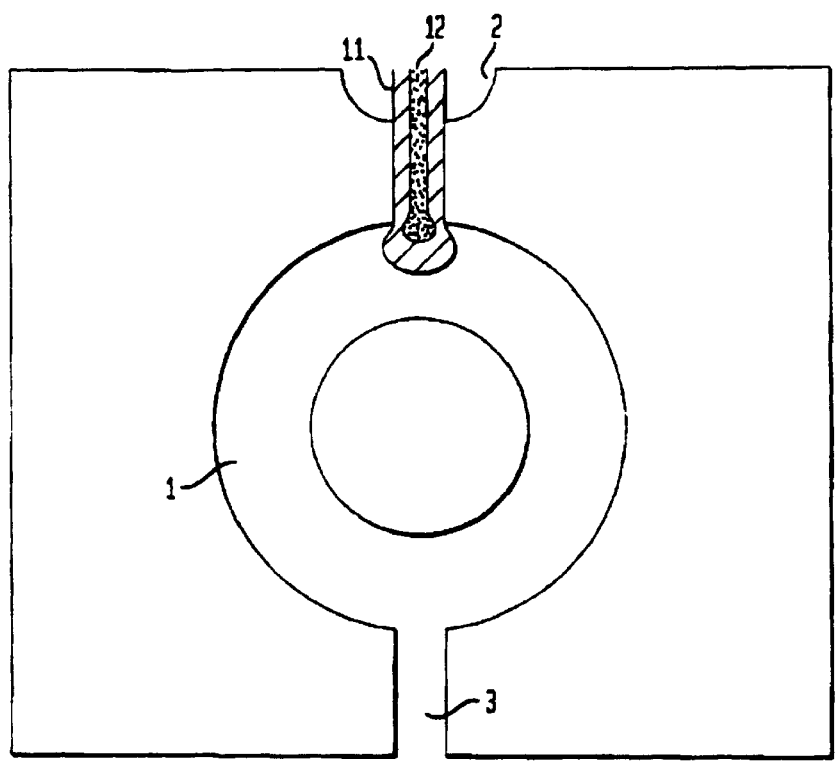
FIG. 3: Material Flow Diagram For Segmented Co-Injected Vaginal Ring (Single Gate)
Figure 3D:
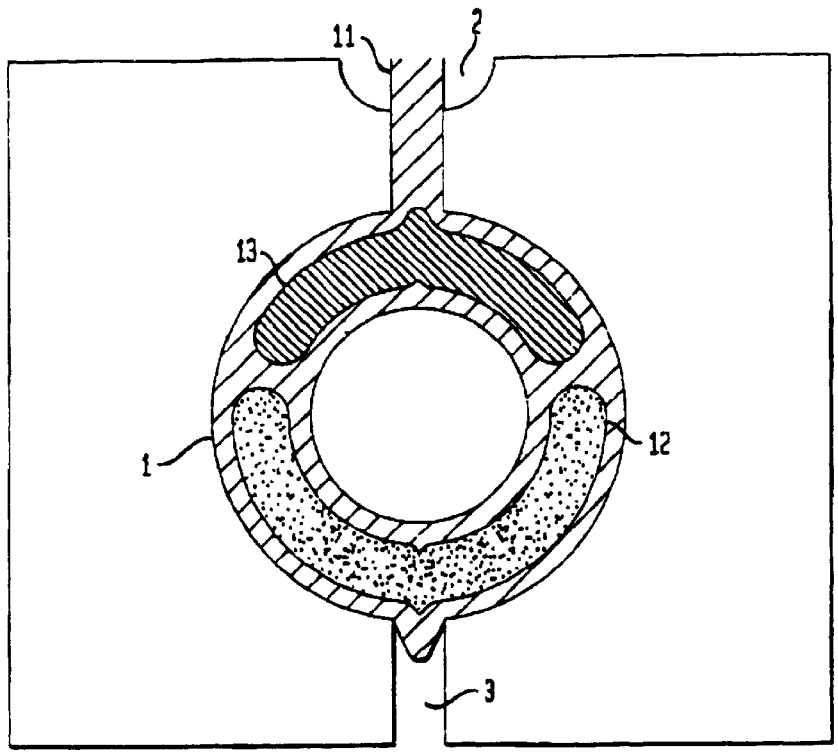

FIG. 3a shows sheath polymer 11 and a first core polymer 12 at time $t_1$, entering entrance runner 2. FIG. 3b illustrates polymer flow at time $t_2$ where sheath polymer 11 and core polymer 12 are proceeding to fill mold cavity. Injection of the first core polymer 12 has been halted and injection of a second core polymer 13 has commenced. The second core polymer may contain a second drug or other active agent different from the one contained in the first core polymer. FIG. 3c illustrates flow at time $t_3$ where first core polymer 12 approaches exit runner 3, and second core polymer 13 is filling that portion of mold cavity 1 not filled by first core polymer 12. FIG. 3d shows the flow at time $t_4$, where injection of second core polymer 13 has been halted and formation of a ring comprising two core polymers surrounded by a sheath has been substantially completed. In an alternate embodiment a second sheath polymer different from sheath polymer 11 may be co-injected with the second core polymer 13, to produce a ring with two distinct drug-containing core regions, each surrounded by a separate sheath of different polymer compositions.

Figure 4A:
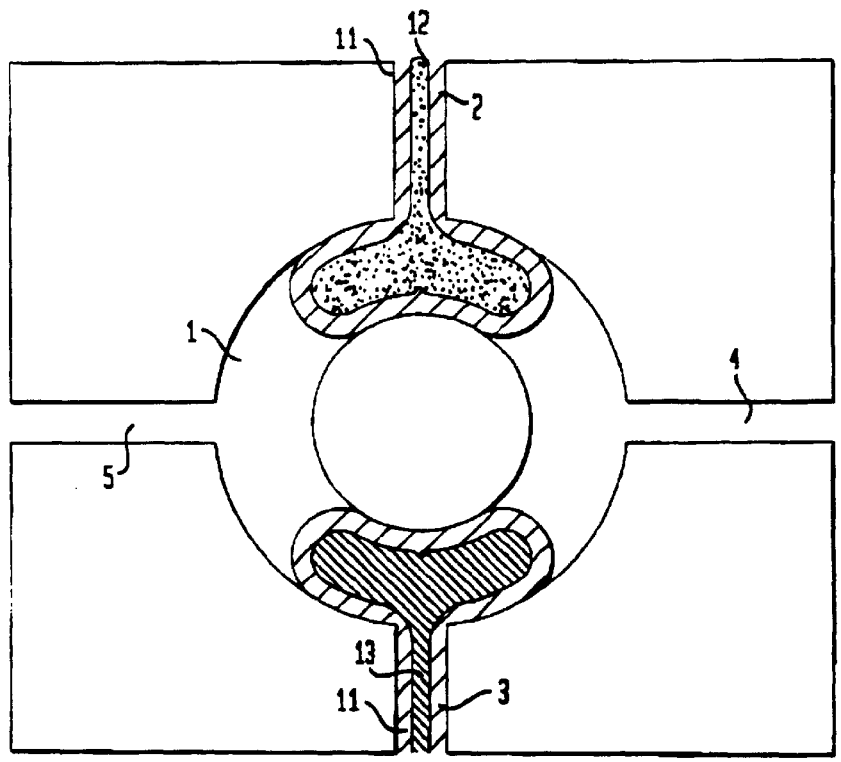
FIG. 4: Material Flow Diagram For Segmented Co-Injected Vaginal Ring (Double Gate)
Figure 4B:
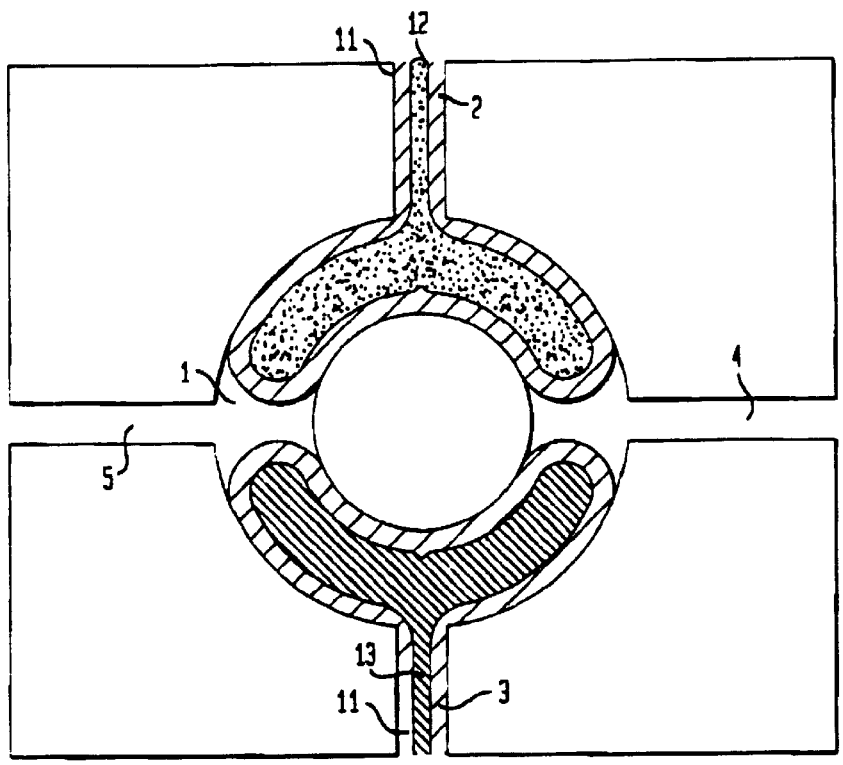
Figure 4C:
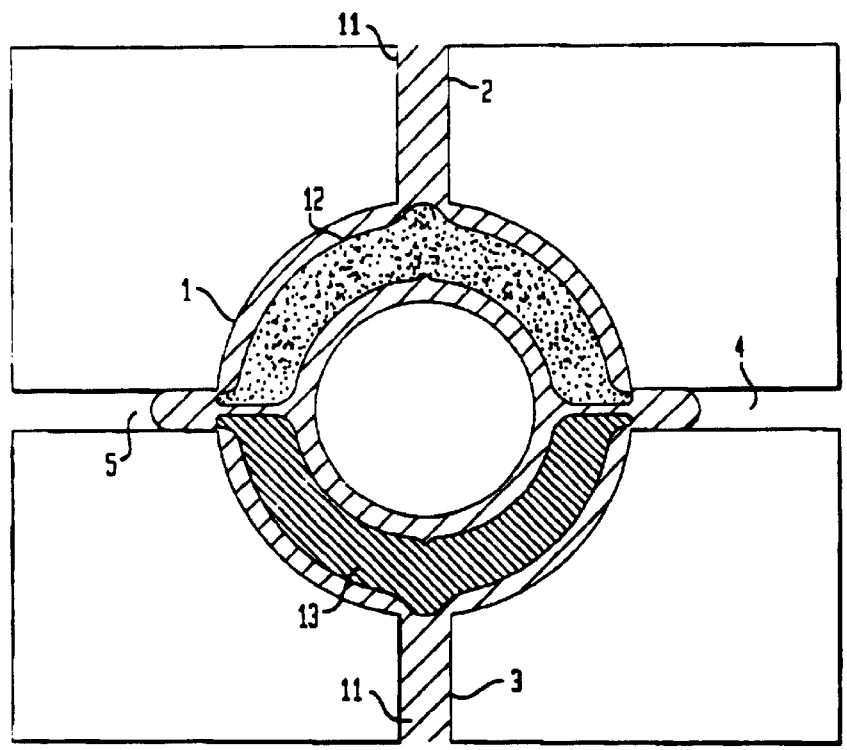

FIG. 4a shows a mold in top planar view, with mold cavity 1 having first entrance gate 2, second entrance gate 3, first exit runner 4, and second exit runner 5. The figure illustrates a flow at time $t_1$, where a sheath polymer 11 and first core polymer 12 are being injected through entrance gate 2, while sheath polymer 11 and second core polymer 13 are being injected through entrance gate 3, into mold cavity 1. FIG. 4b shows the flow at time $t_2$ where sheath polymer 11 and first core polymer 12 and second core polymer 13 are approaching exit runners 4 and 5. FIG. 4c shows the flow at time $t_3$ where sheath polymer 11 proceeds through exit runners 4 and 5, and formation of a ring having two core polymers is substantially complete. In an alternative embodiment, a second sheath polymer different from sheath polymer 11 may be injected through entrance gate 3 with the second core polymer, to produce a ring with two distinct drug containing core regions, each surrounded by a separate sheath of different polymer compositions.

Figure 5A:
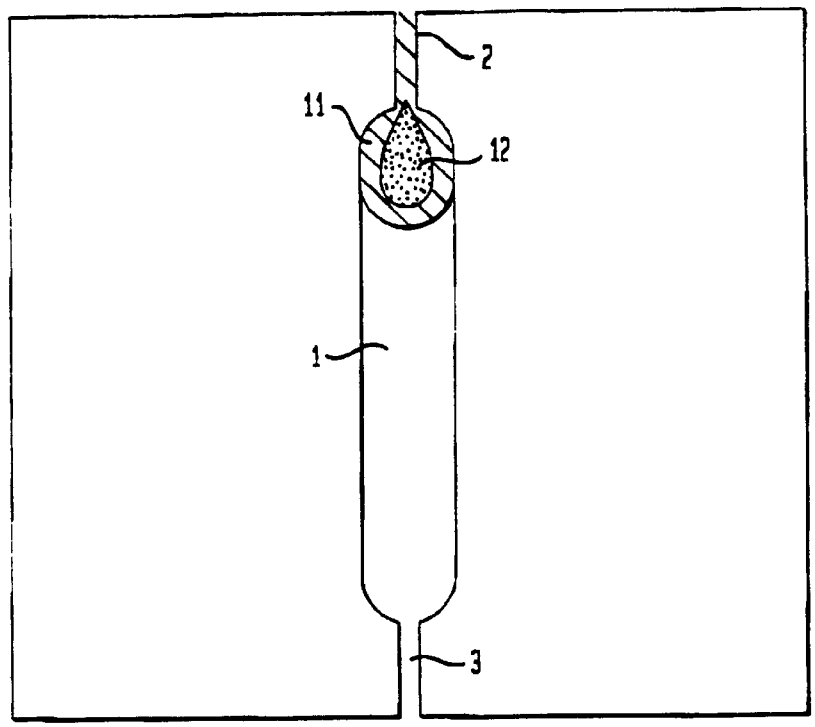
FIG. 5: Material Flow Diagram For Co-Injected Rod
Figure 5B:
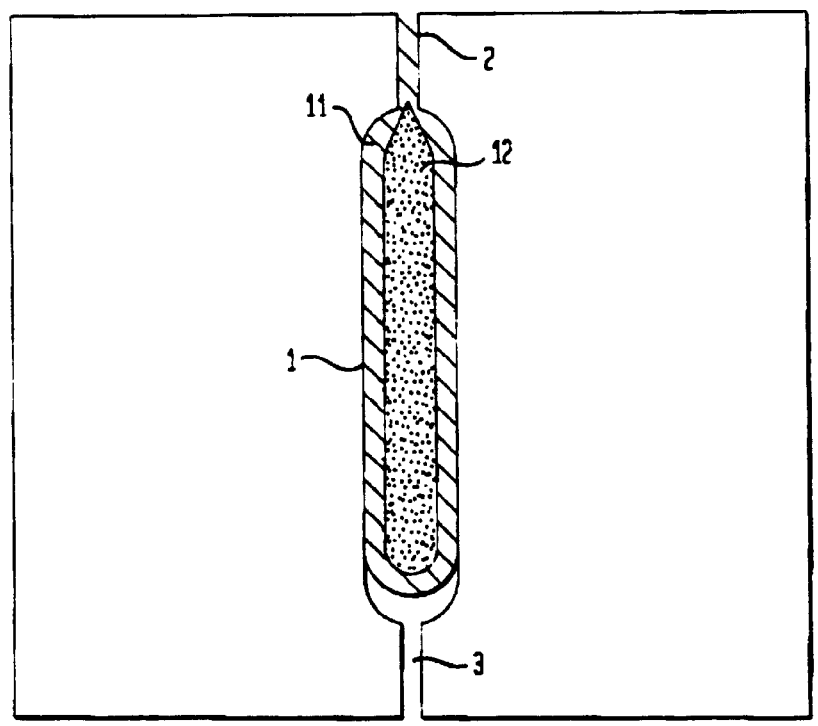
Figure 5C:
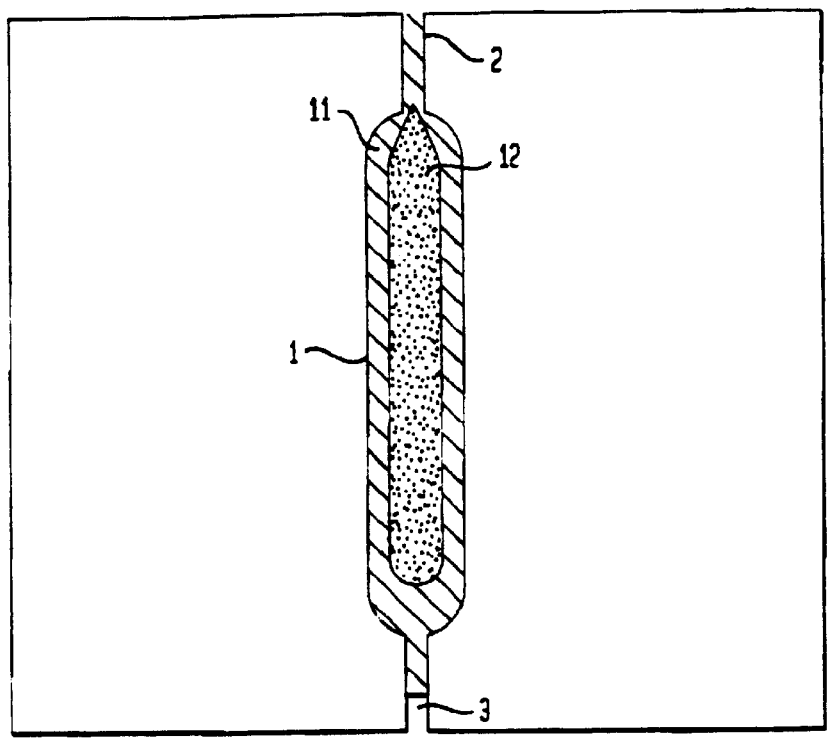
Figure 5D:
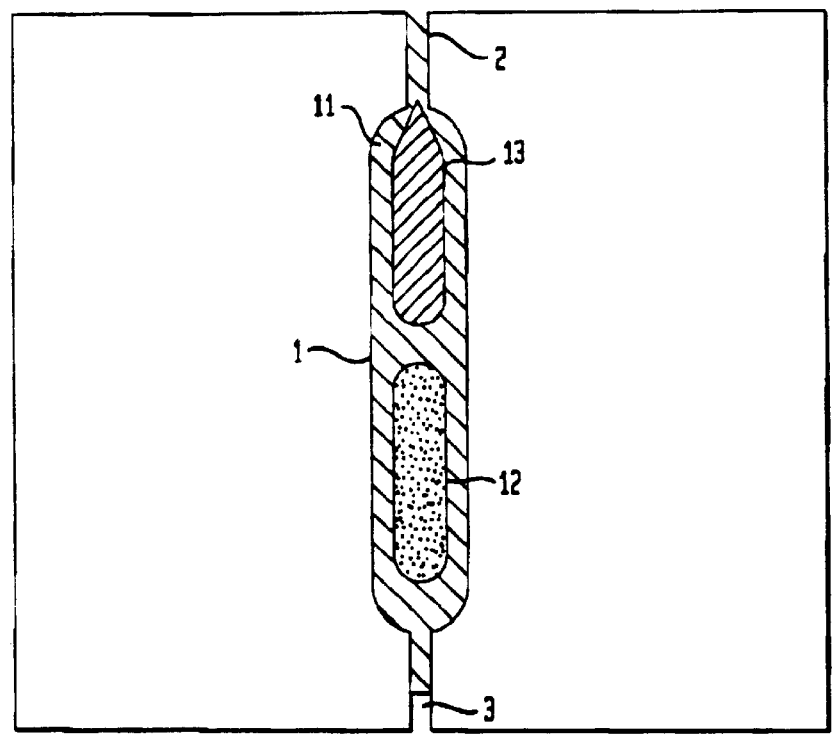

FIG. 5a shows a mold in top planar section having a cylindrical mold cavity 1 with entrance gate 2 and exit runner 3. At time $t_1$, sheath polymer 11 and core polymer 12 are being co-injected through entrance gate 2 into mold cavity 1. FIG. 5b shows the flow at time $t_2$ where sheath polymer 11 and core polymer 12 approach exit runner 3. FIG. 5c shows flow at time $t_3$ where sheath polymer 11 exits through exit runner 3 and formation of a cylindrical rod having a core polymer surrounded by a sheath polymer is substantially complete. FIG. 5d shows a cylindrical rod wherein a first core polymer 12 has been injected for an interval of time, then halted. Subsequently, a second core polymer 13 has been injected, resulting in a rod having two core polymers in distinct segments.

Due to the fluid dynamics of the co-injection process, devices manufactured by co-injection may not have a perfectly uniform membrane thickness over the entire surface area of the completed device. This is especially true for the region of the device near the entrance gates and exit runners. A controlled release device fabricated using stepwise methods, for example, by injecting a reservoir material into a hollow shell, or by application of a membrane around a solid reservoir, or by using a sequential insert molding technique whereby a solid reservoir is coated with membrane material in one or more steps, will have a very uniform membrane thickness over the entire surface area of the finished device. Various sections of such devices will display nearly identical cross-sectional profiles and a very consistent membrane thickness. For example, devices manufactured by sequential insert molding techniques typically exhibit membrane thickness uniformity of ±1%. Also, hollow shells produced by first extruding a shell tubing typically exhibit a membrane thickness uniformity of ±5%. These type of membrane thickness uniformity variations are the result of random process variables and may vary from lot to lot.

Devices manufactured by the co-injection process described herein will usually display variations in membrane thickness which exceed these values, especially in the regions near the gate and runner. These variations may be manifested as either small areas of exposed reservoir material, or smooth transitions in membrane thickness. For example, small areas of exposed reservoir material may occur at the gate if injection of the innermost material is stopped at the same time as, or continues after injection of the outermost material. In these cases the second stream of material is still entering the mold cavity when injection is halted, and following removal of the material in the cured entrance gate, there will be a small exposed area and a region of smooth transition from the exposed area to an area of the device where the membrane thickness is held more constant. Conversely, if both streams of material are started simultaneously, and allowed to exit the mold at the runner site, a similar transition will occur at the runner site. However, by utilizing pulsatile injection, or time delays between the materials, exposure of the reservoir material can be eliminated. If injection of the outermost material is started prior to injection of the inner material, and injection of the inner material is halted prior to the injection of the outermost material, then both the gate and runner regions will not exhibit any exposed inner material. Devices manufactured by co-injection may display regions featuring membrane thickness variations as the injection flow transitions from an area where the fluid dynamics are rapidly changing to one where the fluid flow dynamics are relatively stable and uniform.

Figure 6:
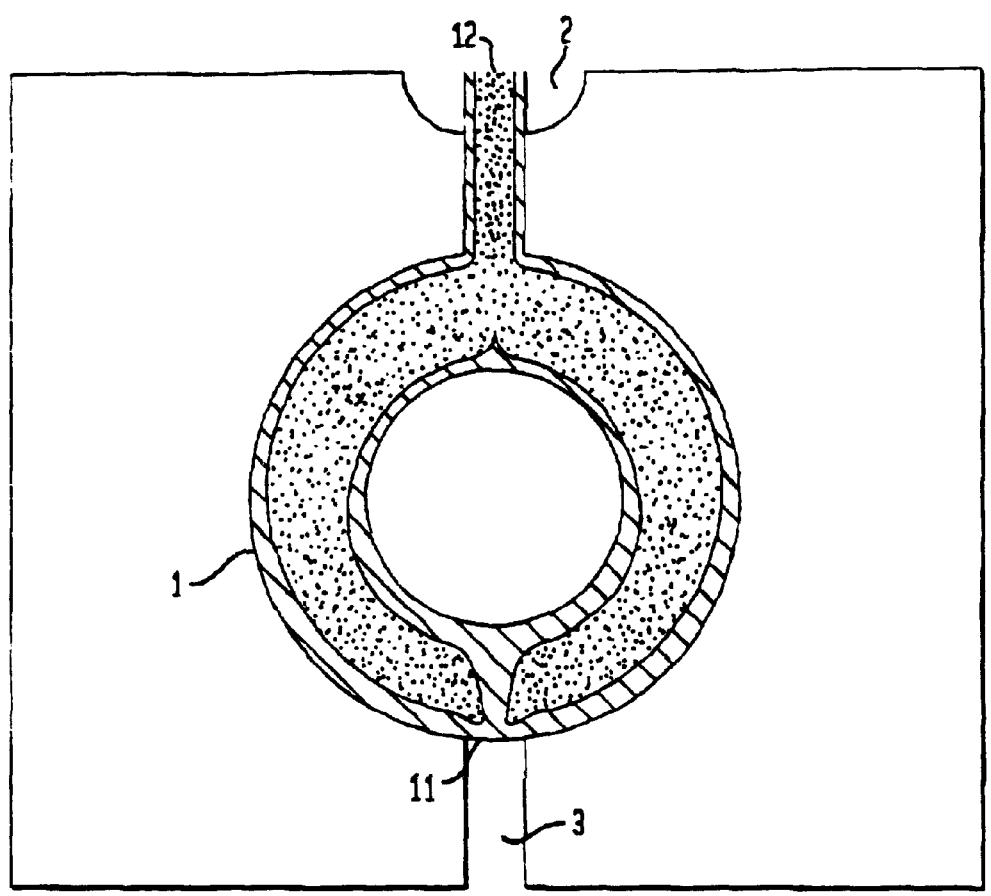
FIG. 6: Intravaginal Ring With Sheath of Variable Thickness

Additionally, a device manufactured by the co-injection technique described herein will typically have a sheath which is relatively thin in one area and which increases in thickness in substantially uniform fashion to an area which is relatively thicker. As a consequence of the fluid dynamics inherent in the co-injection process, areas of the sheath polymer nearest the mold entrance gates will gradually become thinner as core polymer proceeds past, while areas of the sheath polymer nearest the first portion of the core to enter the mold, on the "front" of the core, will substantially retain its initial thickness. The resulting sheath will vary in thickness along its length or circumference. The thickness will increase substantially uniformly from a thin area to a thick area. FIG. 6 illustrates a toroidal mold with entrance gate 2 and exit runner 3, containing an intravaginal ring comprising sheath polymer 11 and core polymer 12. The sheath polymer is thinner near the entrance gate and thicker near the exit runner. The thickness of the sheath increases gradually and uniformly from the thin to the thick area. A ring made in the mold having more than one entrance gate and exit runner, such as in FIGS. 4a–c, would likewise exhibit a sheath with multiple thin areas near the entrance gates, multiple thick areas near the exit runners, and gradually increasing thickness from each thin area to each adjacent thick area. The thickness of the sheath may vary such that the ratio of the thickness of the thickest portion to the thinnest portion may fall anywhere within the range of 1:1 to 10:1.

Cylindrical rods may also be co-injection molded from more than one sheath polymer and more than one active agent. A second sheath polymer and a second active agent may be sequentially injected or alternatively, simultaneously injected through two separate mold gates into a cylindrical mold in the same manner as described for co-injection into a toroidal mold.

Machines for injection molding of thermoset materials are well-known in the art. Silicone polymer containing an active agent was placed in a cartridge tube which is placed on the machine for dispensing the polymer. The machine is adapted with an injection cylinder which draws a measured amount of polymer from the cartridge tube and injects it through a nozzle into the mold. The machine is capable of being adjusted to vary and control the volume of polymer to be dispensed, the pressure and speed at which polymer is injected, and the mold temperature.

In all of the following examples, silicone elastomers were used. Silicone elastomer suppliers are well known in the art. The silicones are available as two-part systems, with one part containing a platinum based catalyst and the other part containing a cross-linking agent. Typical two-part systems require mixing equal parts of silicone without catalyst and silicone containing catalyst in accordance with the manufacturer's instructions, prior to drug addition and the injection molding process.

In each example, the coating or sheath material comprises only silicone polymer. The two parts, one containing catalyst and one containing cross-linker, were mixed together and then vacuumed to remove air prior to placing in a syringe. For drug-containing core polymer, the two-part polymer was first mixed and vacuumed. Hormone was then added and the polymer mixed again. Core polymer containing the drug was then placed in a cartridge tube which is then attached to the injection machine.

EXAMPLE 1

Vaginal rings with a core containing estradiol were produced using a sequential, two nozzle co-injection method. First, 4 cc of drug-free, 25 durometer, low consistency molding grade silicone elastomer was injected with a syringe into a toroidal mold of 55 mm outer diameter and 9 mm cross-sectional diameter heated to 100° C. Following a 10 second time delay, approximately 8 cc of the same silicone elastomer containing 4% estradiol by weight was injected into the mold over a period of 5 seconds, using a standard single component injection nozzle. The materials were cured in the mold for 2–3 minutes before the fully polymerized ring was removed. Twelve rings were produced by this method. The rings had an outer diameter of about 55 mm, and a cross-section of about 9 mm. Dissection of the ring revealed that a drug-free membrane having a mean thickness of approximately 500 microns was applied. Table 1 shows the in-vitro release of estradiol from these twelve rings over a 42 day period. In vitro release of the rings was conducted in a USP dissolution apparatus. Mean daily release after 30 days was 92 $\mu$g/day, with a coefficient of variation of 10%.

TABLE 1

Delivery Rate of Estradiol From High-Dose Co-Injected Rings

| Day | Estradiol Release ($\mu$g/day) | Standard Deviation (N = 12) |
| --- | --- | --- |
| 1 | 146 | 11 |
| 2 | 112 | 7 |
| 3 | 108 | 10 |
| 4 | 104 | 10 |
| 7 | 98 | 9 |
| 8 | 99 | 8 |
| 9 | 101 | 9 |
| 11 | 98 | 9 |
| 15 | 93 | 9 |
| 22 | 94 | 9 |
| 30 | 93 | 9 |
| 36 | 89 | 10 |
| 42 | 90 | 9 |

EXAMPLE 2

A lower dosage strength of the estradiol ring was produced using the same co-injection method as Example 1. However, in this experiment the mold cavity was first completely filled with 9–10 cc of the same drug-free elastomer before injection of the elastomer containing 4% estradiol. A 30 second delay was used prior to injection of the estradiol containing elastomer. Three rings were produced by this method. The rings had the same outer dimensions as those produced in Example 1. Dissection of these rings revealed that a drug-free membrane having a mean thickness of approximately 2 mm was applied. Table 2 shows in-vitro release of estradiol from these three rings over a 28 day period. Mean daily release after 28 days was 38 $\mu$g/day.

TABLE 2

Delivery Rate of Estradiol From Low-Dose Co-Injected Rings

| Day | Estradiol Release ($\mu$g/day) | Standard Deviation (N = 3) |
| --- | --- | --- |
| 1 | 165 | 109 |
| 2 | 66 | 42 |
| 3 | 52 | 29 |

TABLE 2-continued

Delivery Rate of Estradiol From Low-Dose Co-Injected Rings

| Day | Estradiol Release (μg/day) | Standard Deviation (N = 3) |
|---|---|---|
| 4 | 63 | 26 |
| 5 | 48 | 19 |
| 7 | 48 | 18 |
| 9 | 47 | 13 |
| 14 | 40 | 5 |
| 28 | 38 | 5 |

EXAMPLE 3

Another high dosage strength of the estradiol ring was produced using the same co-injection method as Example 1. However, in this experiment a different silicone elastomer was utilized. A 40 durometer liquid silicone elastomer was used and three rings were manufactured using the same conditions as described in Example 1. The rings had an outer diameter of about 55 mm, and a cross-section of about 9 mm. Dissection of the ring revealed that a drug-free membrane having a mean thickness of approximately 510 microns was applied. Table 3 shows the in-vitro release of estradiol from these three rings over a 31 day period. Mean daily release after 31 days was 130 μg/day.

TABLE 3

Delivery Rate of Estradiol From High-Dose Co-Injected Rings

| Day | Estradiol Release (μg/day) | Standard Deviation (N = 3) |
|---|---|---|
| 1 | 304 | 30 |
| 2 | 173 | 41 |
| 3 | 167 | 41 |
| 4 | 158 | 39 |
| 6 | 158 | 41 |
| 8 | 150 | 33 |
| 10 | 146 | 41 |
| 17 | 139 | 33 |
| 24 | 141 | 31 |
| 31 | 130 | 31 |

EXAMPLE 4

Twelve vaginal rings having a core of progesterone consisting of 40% progesterone and 60% silicone were produced. The rings were made at a mold temperature of 120° C. The coating material in an amount of 3 cc was injected into the mold using a syringe. After a 10–15 second time delay, the core material was then injected into the mold until the material visibly exited the mold. The ring was cured for 10 minutes at 120° C. The rings had an outer diameter of about 55 mm, and a cross-section of about 9 mm. The average weight of the progesterone rings was 9 grams with an average coating thickness of 512 microns. Table 4 shows the in-vitro release of progesterone from these twelve rings over a 28 day period. Mean daily release after 28 days was 10.2 mg/day.

TABLE 4

Delivery Rate of Progesterone From Co-Injected Rings

| Day | Progesterone Release (mg/day) | Standard Deviation (N = 12) |
|---|---|---|
| 1 | 70.4 | 5.0 |
| 2 | 33.8 | 2.5 |

TABLE 4-continued

Delivery Rate of Progesterone From Co-Injected Rings

| Day | Progesterone Release (mg/day) | Standard Deviation (N = 12) |
|---|---|---|
| 3 | 27.1 | 2.2 |
| 4 | 21.4 | 2.5 |
| 5 | 21.5 | 1.9 |
| 6 | 18.1 | 1.6 |
| 7 | 17.3 | 1.8 |
| 14 | 15.7 | 1.4 |
| 21 | 12.2 | 0.9 |
| 28 | 10.2 | 0.9 |

EXAMPLE 5

The core material of these rings consisted of 14% medroxyprogesterone acetate (MPA), 4% estradiol, and 82% of silicone. The coating material consisted of only silicone. Twelve rings were made at a mold temperature of 135° C. The coating material in an amount of 3 cc was injected into the mold using a syringe. The core material was then injected into the mold until the material visibly exited the mold. The time delay between the first and second injection was approximately 30 seconds. The ring was cured for 5 minutes at 135° C. The rings had an outer diameter of about 55 mm, and a cross-section of about 9 mm. Dissection of the ring revealed that a drug-free membrane having a mean thickness of approximately 490 microns was applied. The average weight of the estradiol and MPA homogeneous rings was 9. Table 5 shows the in-vitro release of estradiol and MPA from these twelve rings over a 21 day period. Mean daily release after 21 days was 189 μg/day estradiol and 2.0 mg/day MPA.

TABLE 5

Delivery Rate of MPA and Estradiol From Homogenous Co-Injected Rings

| Day | Estradiol Release (μg/day) | MPA Release (mg/day) |
|---|---|---|
| 1 | 642 | 5.2 |
| 2 | 315 | 4.0 |
| 3 | 274 | 3.3 |
| 4 | 254 | 2.8 |
| 5 | 233 | 2.8 |
| 6 | 251 | 2.4 |
| 7 | 189 | 2.3 |
| 14 | 216 | 2.3 |
| 21 | 189 | 2.0 |

EXAMPLE 6

Six segmented vaginal rings were produced having estradiol in approximately one-half of the circumferential length of the ring, and a combination of estradiol and progesterone in the other half. The estradiol core material consisted of 4% estradiol and 96% silicone, and the estradiol/progesterone core consisted of 4% estradiol and 40% progesterone and 56% silicone. The coating material consisted only of silicone. The rings were made at a mold temperature of 120° C. The coating material in an amount of 3 cc was injected into the mold. The process took approximately 20 seconds. The estradiol/progesterone core material was injected for 10 seconds before stopping. After a one minute time delay, the second core material containing estradiol was then injected into the mold in the amount of 4 cc over a 30 second period.

The rings were cured for 10 minutes. The rings had an outer diameter of about 55 mm, and a cross-section of about 9 mm. Dissection of the ring revealed that a drug-free membrane having a mean thickness of approximately 420 microns was applied. Table 6 shows the in-vitro release of estradiol and progesterone from these six rings over a 33 day period. Mean daily release after 33 days was 165 µg/day estradiol and 3.9 mg/day progesterone.

TABLE 6

Delivery Rate of Estradiol and Progesterone From Segmented Co-Injected Rings

| Day | Estradiol Release (µg/day) | Progesterone Release (mg/day) |
| --- | --- | --- |
| 1 | 1653 | 27.8 |
| 2 | 585 | 13.9 |
| 5 | 317 | 9.8 |
| 6 | 243 | 8.0 |
| 7 | 252 | 8.0 |
| 13 | 186 | 5.2 |
| 20 | 199 | 5.4 |
| 28 | 194 | 4.2 |
| 33 | 165 | 3.9 |

What is claimed is:

1. A co-injection method for producing a controlled release device which comprises a thermoset polymer core containing at least one releasable active agent surrounded by a thermoset polymer sheath, the method comprising of injecting a first thermoset polymer and a second thermoset polymer containing at least one active agent into a mold cavity.

2. The method of claim 1, wherein at least one of the first polymer and the second polymer comprises a silicone polymer.

3. The method of claim 1, wherein the first and second polymer are injected sequentially.

4. The methods of claim 1, wherein the first and second polymer are injected simultaneously.

5. The method of claim 4, wherein the simultaneous injection of the first and second silicone polymers is preceded by injection of the first silicone polymer solely.

6. A method for producing a device for controlled release of an active agent, comprising:
   i) injecting a first thermoset polymer into a mold cavity and effecting at least partial cross-linking of the first polymer;
   ii) injecting a second thermoset polymer containing the active agent into the mold.

7. A method for producing a device for controlled release of a plurality of active agents, comprising:
   i) injecting a first thermoset polymer into a mold cavity and effecting at least partial cross-linking of the first polymer;
   ii) injecting a second thermoset polymer containing a first active agent into the mold;
   iii) after injecting the second polymer, injecting a third thermoset polymer containing a second active agent into the mold.

8. The method of claim 7, wherein the first, second and third thermoset polymers may be the same or different.

9. The method of claim 7, wherein at least one of the active agents is a therapeutic drug, peptide or prodrug.

10. The method of claim 9, wherein at least one of the therapeutic drugs is a hormone.

11. A method of producing a device for controlled release of a plurality of active agents, in a mold cavity having a plurality of injection gate openings, comprising:

i) injecting for a first time interval, a first thermoset polymer into the mold cavity through a first gate opening, and a second thermoset polymer through a second gate opening,
   ii) injecting, for a second time interval, thermoset polymer containing a first active agent into the mold cavity through the first gate opening, and thermoset polymer containing a second active agent through the second gate opening.

12. The method of claim 11, wherein any of the polymers may be the same as or different from any of the other polymers.

13. The method of claim 11, wherein at least one of the polymers is a silicone polymer.

14. A toroidal ring produced in accordance with any of claims 1, 6, 7, or 11 for controlled release of at least one active agent comprising a core of thermoset polymer containing the active agent, surrounded by a thermoset polymer sheath.

15. A cylindrical rod produced in accordance with any of claims 1, 6, 7, or 11 for controlled release of at least one active agent comprising a core of thermoset polymer containing the active agent(s), surrounded by a thermoset polymer sheath.

16. A controlled release device produced by any of the preceding claims 7 or 11 comprising at least a first thermoset polymer containing a first releasable active agent, and a second thermoset polymer containing a second releasable active agent, surrounded by a thermoset polymer sheath.

17. A controlled release device comprising a core of thermoset polymer containing at least one active agent surrounded by a thermoset polymer sheath of non-uniform thickness.

18. The controlled release device of claim 17 wherein said sheath comprises a first thermoset polymer and said polymer containing at least one active agent comprises a second thermoset polymer and wherein said first polymer is the same as or different from said second polymer.

19. The controlled release device of claim 18 wherein at least one of said first thermoset polymer and said second thermoset polymer comprises a silicone polymer.

20. The controlled release device of claim 18 wherein said sheath and said core are formed by co-injecting said first thermoset polymer and said second thermoset polymer into a mold cavity of a mold.

21. The controlled release device of claim 20 wherein said first thermoset polymer and said second thermoset polymer are injected simultaneously.

22. The controlled release device of claim 20 wherein said first thermoset polymer and said second thermoset polymer are injected sequentially.

23. The controlled release device of claim 22 wherein said first thermoset polymer is injected into said mold cavity and partially crosslinked for a first time interval prior to injecting said second thermoset polymer into said mold cavity.

24. The controlled release device of claim 23 wherein said partial crosslinking is effected by heating said mold.

25. A cylindrical rod comprising a core of thermoset polymer containing at least one active agent, surrounded by a thermoset polymer sheath, wherein the thickness of sheath varies along the length of the rod.

26. A cylindrical rod of claim 25, wherein the sheath is relatively thin at one end of the rod, relatively thicker at an opposite end of the rod, and the thickness of the sheath increases substantially uniformly along the length of the rod from the first end to the opposite end.

27. An intravaginal ring comprising a core of thermoset polymer containing at least one active agent, surrounded by a thermoset polymer sheath, wherein the thickness of sheath varies along the circumference of the ring.

28. An intravaginal ring of claim 27, wherein the sheath is relatively thin on a first area of the ring, relatively thicker on a second area diametrically opposite the thin portion and the thickness of the sheath increases substantially uniformly along the circumference of the ring from the first area to the second area.

29. An intravaginal ring of claim 26, wherein the sheath has multiple areas of relative thinness and multiple areas of relative thickness, and the thickness of the sheath increases substantially uniformly from any one thin area to an adjacent thick area.

30. The intravaginal ring of claim 27 wherein said polymer sheath comprises a first thermoset polymer and said polymer containing at least one active agent comprises a second thermoset polymer.

31. The intravaginal ring of claim 30 wherein at least one of said first thermoset polymer and said second thermoset polymer comprises a silicone polymer.

32. The intravaginal ring of claim 31 said core and said sheath are formed by co-injecting said first thermoset polymer and said second thermoset polymer into a cavity of a mold.

33. The intravaginal ring of claim 32 wherein said first thermoset polymer and said second thermoset polymer are injected simultaneously.

34. The intravaginal ring of claim 33 wherein said first thermoset polymer and said second thermoset polymer are injected sequentially.

35. The intravaginal ring of claim 34 wherein said first thermoset polymer is injected into said mold cavity and partially crosslinked for a first time interval prior to injecting said second thermoset polymer into said mold cavity.

36. The intravaginal ring of claim 35 wherein said partial crosslinking is effected by heating said mold.

* * * * *